(12) United States Patent
Sarbach et al.

(10) Patent No.: US 7,049,149 B2
(45) Date of Patent: May 23, 2006

(54) BIOLOGICAL MARKER FOR STRESS STATES

(75) Inventors: Christian Sarbach, Versailles (FR); Pascal Delvordre, Massy (FR); Eric Postaire, Vanves (FR)

(73) Assignee: AR2I SA - Analyses - Recherches et Innovation Instrumentale, Clamart (FR)

( * ) Notice: Subject to any disclaimer, the term of this patent is extended or adjusted under 35 U.S.C. 154(b) by 0 days.

(21) Appl. No.: 10/494,692

(22) PCT Filed: Oct. 18, 2002

(86) PCT No.: PCT/FR02/03572

§ 371 (c)(1),
(2), (4) Date: Oct. 13, 2004

(87) PCT Pub. No.: WO03/040719

PCT Pub. Date: May 15, 2003

(65) Prior Publication Data

US 2005/0042762 A1    Feb. 24, 2005

(30) Foreign Application Priority Data

Nov. 6, 2001    (FR) .................................. 01 14310

(51) Int. Cl.
*G01N 33/00*    (2006.01)
*G01N 1/22*    (2006.01)

(52) U.S. Cl. ........................ 436/124; 436/56; 436/126; 436/141; 436/161; 436/173; 436/181; 436/900

(58) Field of Classification Search ................. 436/56, 436/124, 126, 141, 161, 174, 177, 181, 900, 436/173; 514/743, 744, 759, 557
See application file for complete search history.

(56) References Cited

U.S. PATENT DOCUMENTS

| 5,996,586 A | * | 12/1999 | Phillips | ....................... 128/898 |
| 6,221,026 B1 | * | 4/2001 | Phillips | ....................... 600/532 |
| 2002/0090664 A1 | * | 7/2002 | Wiegand et al. | ........... 435/7.92 |

FOREIGN PATENT DOCUMENTS

| EP | 1096245 | | 5/2001 |
| JP | 2001-89367 | * | 4/2001 |

OTHER PUBLICATIONS

Phillips et al. Clinical Chemistry, vol. 38, No. 1, 1992, pp. 60-65.*

* cited by examiner

*Primary Examiner*—Maureen M. Wallenhorst
(74) *Attorney, Agent, or Firm*—Michael Best & Friedrich LLP

(57) ABSTRACT

The object of the invention is to propose a novel biomarker for stress states, which biomarker is highly meaningful and capable of enabling quantitative measurements to be made of stress levels. To do this, it has been found, surprisingly, that the air at the end of a person's breathing out, known as "alveolar" air, contains fluorine compounds when that person has been subjected to various stress states. More precisely, the present invention provides components based on fluorine compounds, in particular fluorinated chloroalkanes, used as biomarkers of stress states.

6 Claims, 5 Drawing Sheets

BIOLOGICAL MARKER FOR STRESS STATES

The present invention relates to a biological marker (or biomarker) that reveals stress states, to a method of quantitatively evaluating the presence of said biological marker of stress states, and to the use of such a marker prepared in a packaged form for preventing stress states.

BACKGROUND OF THE INVENTION

The concept of stress states covers those metabolic and/or behavioral reactions that are provoked in an organism as a whole by numerous exogenous aggression factors such as: inflammatory illnesses; surgery; traumatic shocks; solar, electromagnetic, or ionizing radiation; smoking; pollution; allergies; prolonged effort; emotion; cold; etc.

The type of disturbance engendered in the organism enables different types of states of stress to be distinguished, where stress can be of: chemical, microbiological, biochemical, physiological, psychic, biophysical, or pharmacological order.

It is well established that under the effect of some of the above-mentioned factors, the organism produces oxidizing agents that generate a kind of stress referred to as oxidation stress. These agents are in the form of reactive oxygen species (ROS). For example, in the event of prolonged effort, demand for oxygen increases, and consequently oxygen consumption increases, thereby leading both to a state of hypoxia and to overproduction of ROS agents.

The production of ROS agents is then associated with normal endogenous biochemical mechanisms. In particular, in the respiratory system, 2% to 4% of the oxygen involved is reduced incompletely giving rise to ROS agents.

ROS agents are free radicals, atoms, or molecules that are unstable and reactive, usually presenting one or more lone electrons. The main ROS agents are: singlet oxygen (O—), superoxide anion, hydrogen peroxide, hydroxyl radical, nitrogen monoxide, or hydroperoxy radicals (produced during peroxidation of membrane lipids, particularly those constituted by polyunsaturated fatty acids).

Biologically speaking, oxidation stress leads to:

lipid peroxidation targeted on cell membranes and mitochondrial; polyunsaturated fatty acids (PUFA) are attached and released ethane ($\omega$-3 PUFA) and pentane ($\omega$-6 PUFA);

protein oxidation of mitochondrial proteins, leading to malfunction of the respiratory system and to a reduction in the amount of energy produced by cells; or oxidation of mitochondrial DNA (mtDNA) which leads to mutations that also lead to malfunction of the mitochondria.

Oxidation is the main cause of cellular aging and of diseases due to age (cancers, cardiovascular disorders, reduced immune functions, brain malfunction such as Alzheimer's disease, or cataracts). This is corroborated by the fact that anti-oxidant foodstuffs (ascorbic acid, tocopherol, and carotenoids of fruit and vegetables) contribute to combatting the appearance of such degenerative diseases.

Ethane and pentane constitute known biomarkers for oxidation stress states. As mentioned above, oxidation stress gives rise to metabolic disorders including lipid peroxidation which leads to the formation of ethane and pentane. These products are volatile substances which are subsequently eliminated in breathed-out air.

Pentane appears to be more significant than ethane in vivo since, in membranes, lipids of $\omega$-6 PUFA structure predominate over those of $\omega$-3 PUFA structure. The measured ethane/pentane concentration in breathed-out air is proportional to the oxidation stress state.

Nevertheless, it is important to have a quantitative marker for stress states, and in particular for oxidation stress.

OBJECT AND SUMMARY OF THE INVENTION

The object of the invention is thus to propose a novel biomarker of stress states, which is highly significantly and which can enable stress levels to be measured quantitatively.

To do this it has been found, surprisingly, that the air at the end of a person's breathing out, referred to as "alveolar air", contains fluorine compounds if the person has been subjected to various stress states.

More precisely, the present invention provides a product of fluorine compounds used as a biomarker of stress states, in particular compounds based on fluorinated chloroalkanes (also known as CFCs or freons).

More precisely, the product is obtained from a biological fluid, i.e. a liquid or gaseous material produced by the human body, by fractioning and concentrating on final portions of samples of said fluid. The fluid may be constituted, for example, by air that has been breathed out, by blood, or by urine.

Preferably, the product of the invention is contained in a fraction of alveolar air obtained by concentrating air breathed out by the human body. The biomarker is based on at least one of the components selected from: trichloro-trifluro-ethane; tetrachloro-hexafluoro-butane; and trichloro-monofluoro-methane. Since it is the most abundant, it is preferable to select trichloro-trifluro-ethane.

The invention also provides a method of quantitatively evaluating the presence of said marker, the method consisting in taking and concentrating a sample of material, in analyzing the concentrated product by thermal desorption, gas chromatography coupled with a mass spectrometer in order to identify the presence of CFCs, and in particular of $C_2Cl_3F_3$, and then by calibration of the chromatographic peak of the biomarker.

A quantitative determination of a stress level for each stress state can then be performed by calibration, in direct association with the quantitative evaluation of the presence of the biomarker of the invention. The result of such determination can serve as an intermediate base for subsequent medical diagnostic purposes (inflammation, etc. ... ).

The invention also relates to using fluorine compounds limiting fluorine losses and thus losses of fluorine derivatives, prepared as medication or as a food additive, to act as an agent for preventing stress, using an appropriate formulation of the active principle. Such fluorine compounds can be sodium fluorides (e.g. monofluorophosphate), CFCs, fluorine-containing amino acids and derivatives thereof (e.g. amine fluoride, etc.).

Such compounds can be administered under a variety of forms: tablets, an ancillary compound for a medical device such as a patch or a dressing, or indeed as a liquid formulation additive in an ionophoretic device for percutaneous administration.

BRIEF DESCRIPTION OF THE DRAWINGS

Other characteristics and advantages will appear on reading the following detailed description relating to embodiments of the invention for different stress states given with reference to the accompanying figures, in which, respectively.

MORE DETAILED DESCRIPTION

The device for sampling breathed-out air as used for performing the measurements described below is of the type described in the patent application published under the No. FR 2 800 465, filed in the name of the Applicant and incorporated by reference. That device enables air at the end of breathing out, known as "alveolar air" to be taken and concentrated, which air contains a rich fraction of biomarkers present in pulmonary air, is highly sensitive, and presents a high level of reproducibility between samples. Common protocols relating to conditions for applying stress and for taking samples of air were complied with in the various examples described below, in order to verify that the results are reproducible.

The samples that were taken were in the form of cartridges filled with two layers of adsorbent material. The various samples were analyzed by thermal desorption, followed by gas chromatography with detection by mass spectrometry.

The chemical family of fluorinated chloroalkanes, also referred to as chloro-fluoro-carbons (CFCs) or freons, were thus measured as biomarkers for stress in the breathed-out alveolar air. In the examples that follow, tri-chloro-trifluoroethane $C_2Cl_3F_3$ is the biomarker that shows up most particularly.

The chemical structure of this biomarker was determined by mass spectrometry associated with gas chromatography.

The examples of increases in the production and in the elimination of the biomarker of the invention as illustrated below were caused by various different types of stress.

Figure 1:
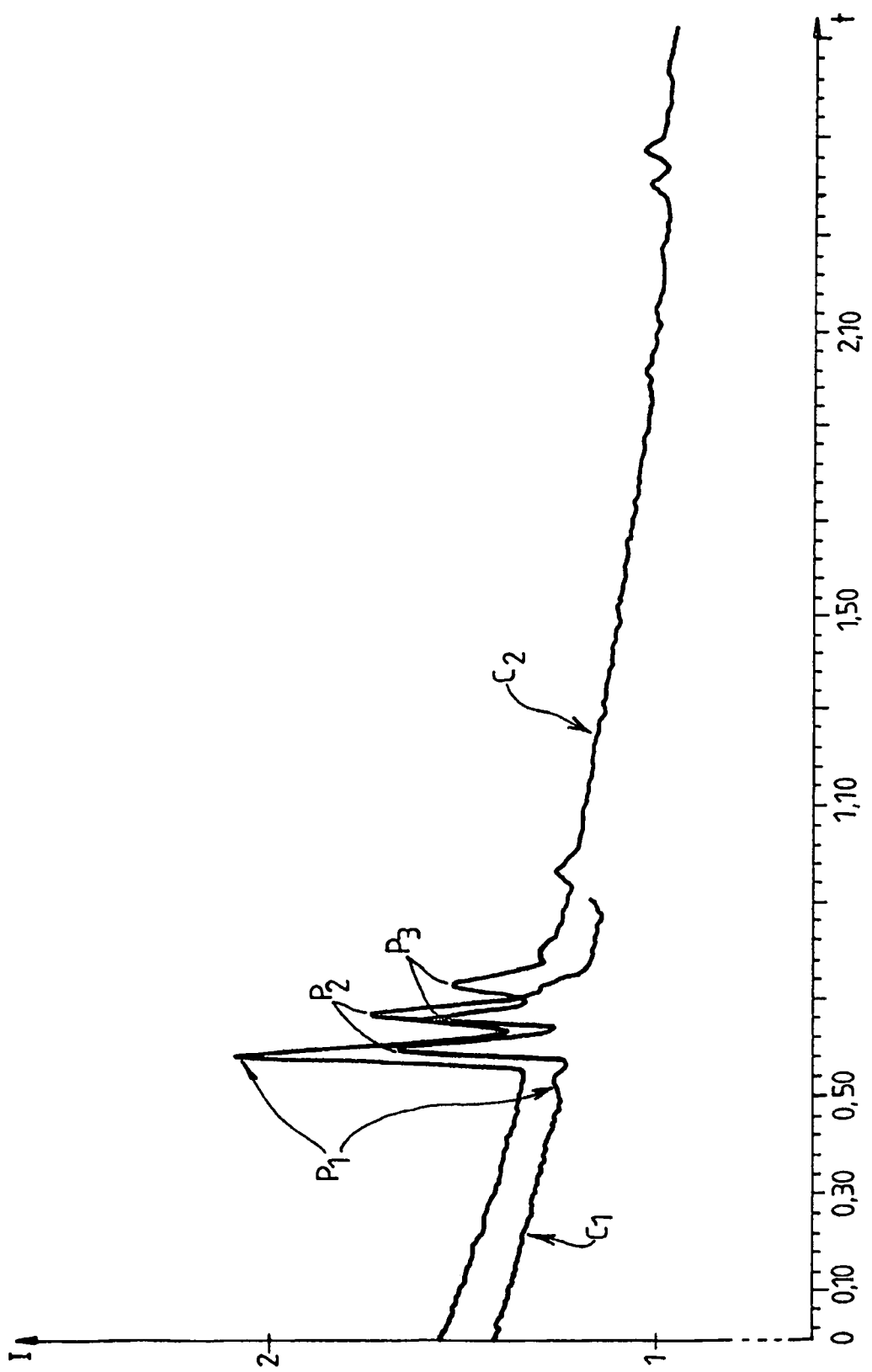
FIG. 1 shows two chromatograms of alveolar air sampled on a person respectively at rest and after walking fast for 15 minutes.

With reference to FIG. 1, moderate effort was used to illustrate physiological stress. The two chromatograms shown, C1 and C2, correspond to chromatographic analysis of the alveolar air sampled on the same person respectively at rest (curve C1) and after walking fast for 15 minutes (fragmentary curve C2). The intensity I of the signal is plotted as a function of time t. The units are arbitrary. The two chromatograms are slightly offset in order to improve the visibility of the figure.

The peaks P1 correspond to the presence of $C_2Cl_3F_3$, the peaks P2 to the presence of isoprene, and the peaks P3 to the presence of dichloromethane. The difference in intensity between the peaks P1 shows clearly that $C_2Cl_3F_3$ is sensitive as a biomarker for stress of the physiological type.

Figure 2:
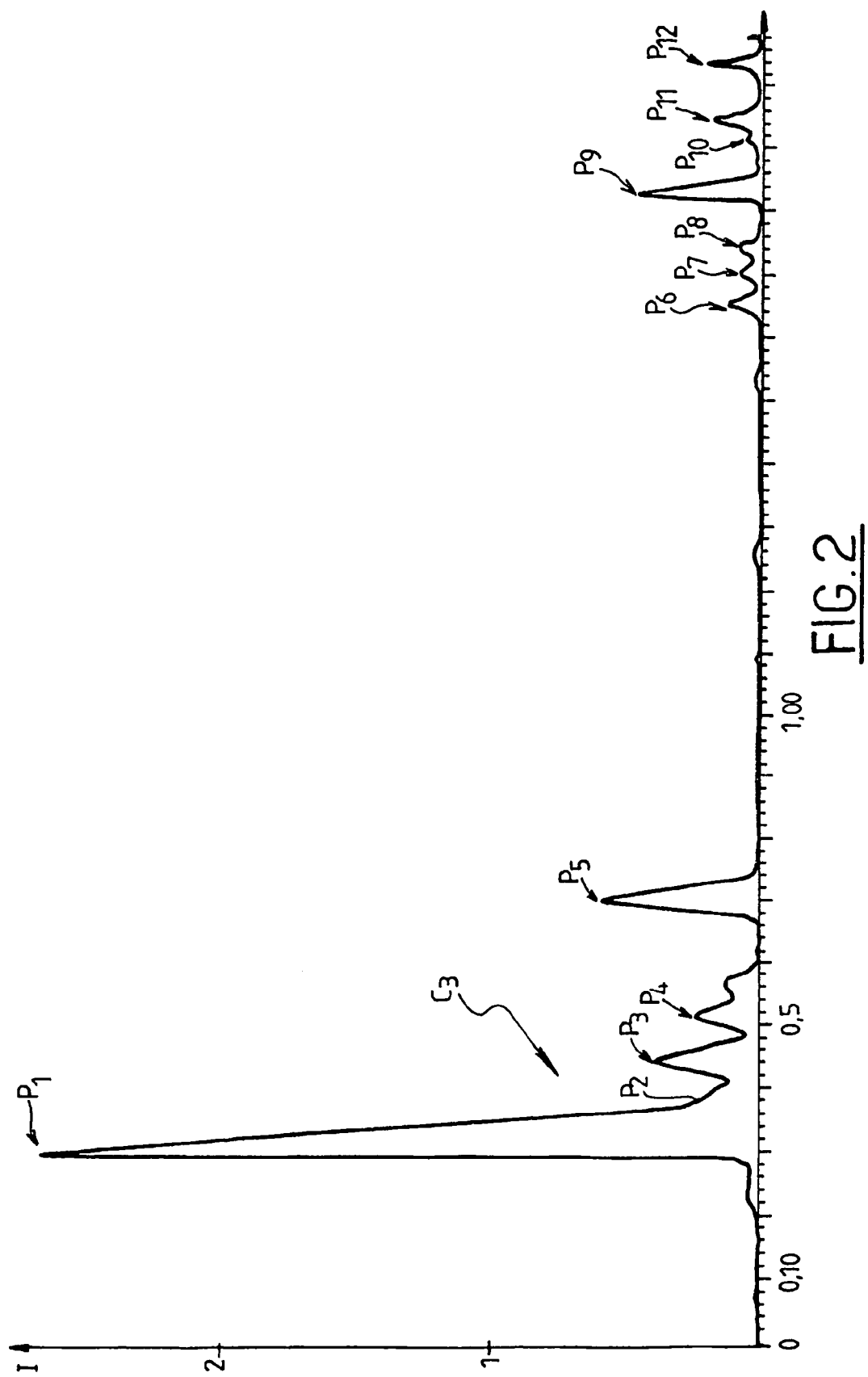
FIG. 2 is a chromatogram of alveolar air sampled on a person 5 minutes after intensive sports effort undertaken for 1 hour.
Figure 3:
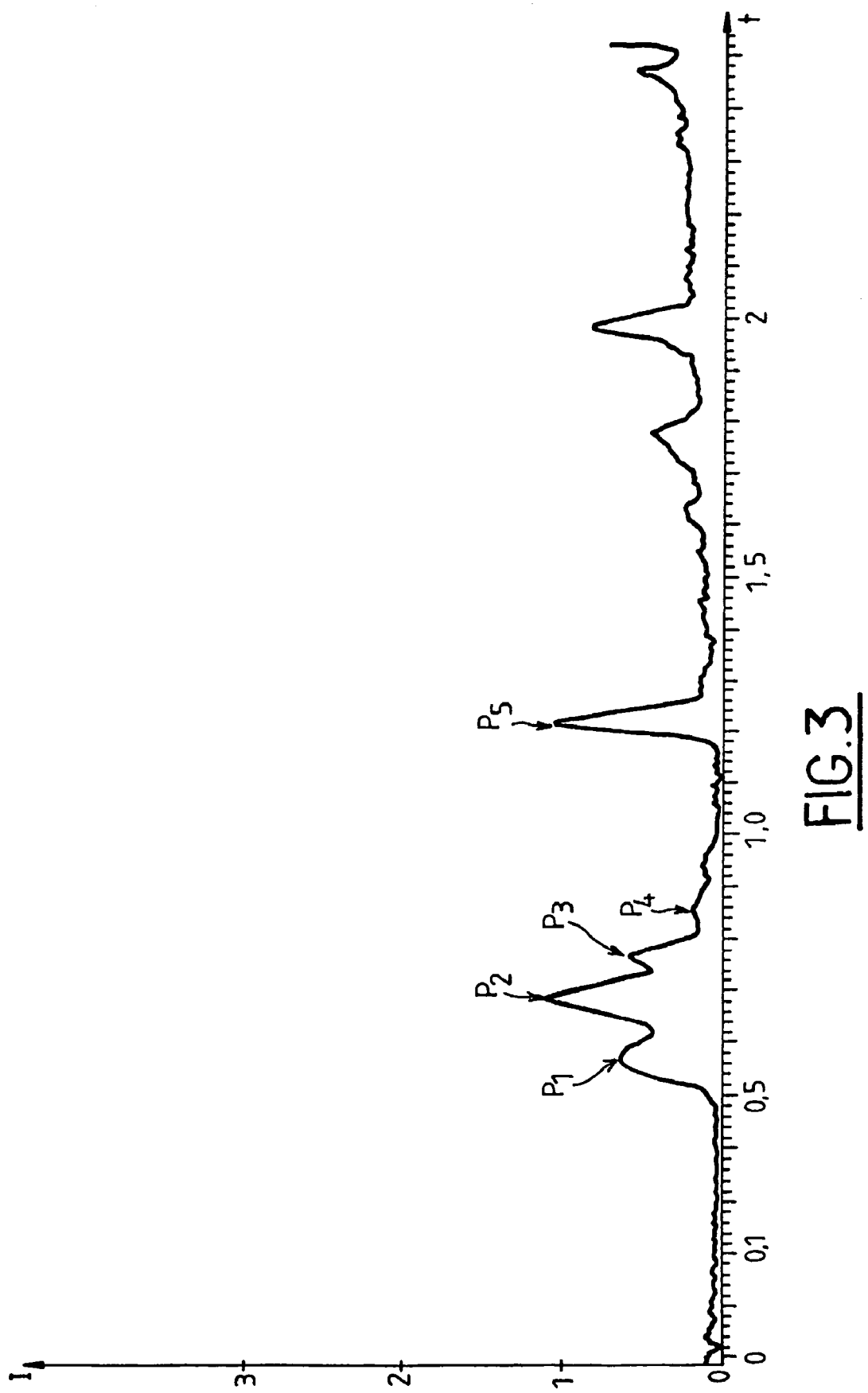
FIG. 3 is a chromatogram of alveolar air taken from the same person 6 hours after the intense sports effort.

FIGS. 2 and 3 relate to effort causing the person to be out of breath, caused by playing tennis for 1 hour, and is likewise for the purpose of illustrating physiological stress.

In FIG. 2, the chromatogram C3 of alveolar air was taken from the person 5 minutes after the sports effort. The high amplitude of the peak P1 represents the level of stress to which the organism of the player was subjected. The peaks P4 to P12 correspond respectively to cyclohexane (P4), to hexane (P5), to chloroform (P6), to methylcyclohexane (P7), to trimethylhexane (P8), to heptane (P9), to tetrachloroethylene (P10), to benzene (P11), and to ethylether (P12).

In FIG. 3, i.e. 6 hours after the intensive sports effort, the peak P1 of the chromatogram C4 has diminished significantly, thereby further illustrating the dedicated stress biomarker function associated with trichlorotri-fluoroethane $C_2Cl_3F_3$.

Figure 4:
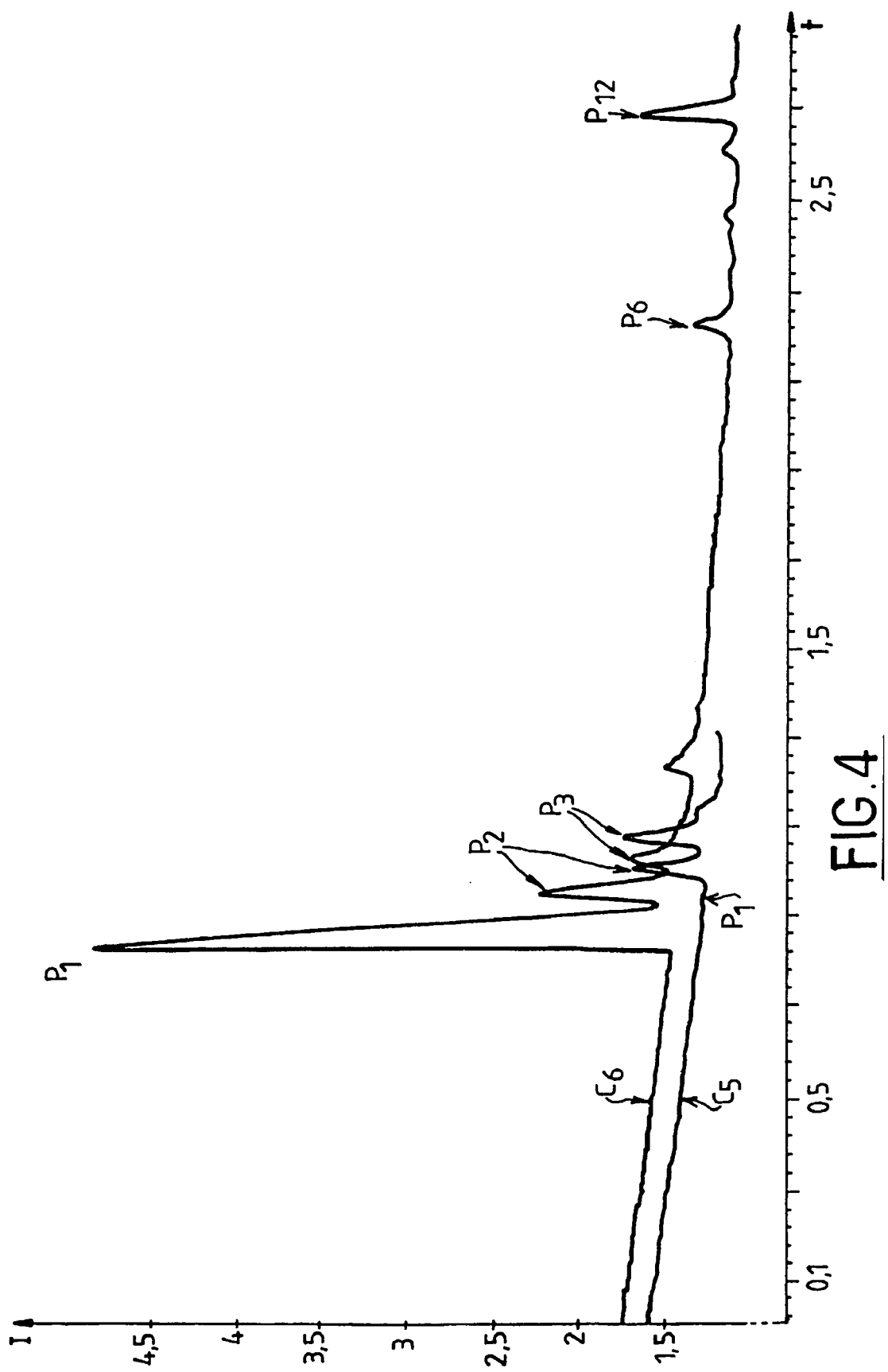
FIG. 4 is two chromatograms of alveolar air taken from an occasional smoker respectively at rest and 5 minutes after smoking.
Figure 5:
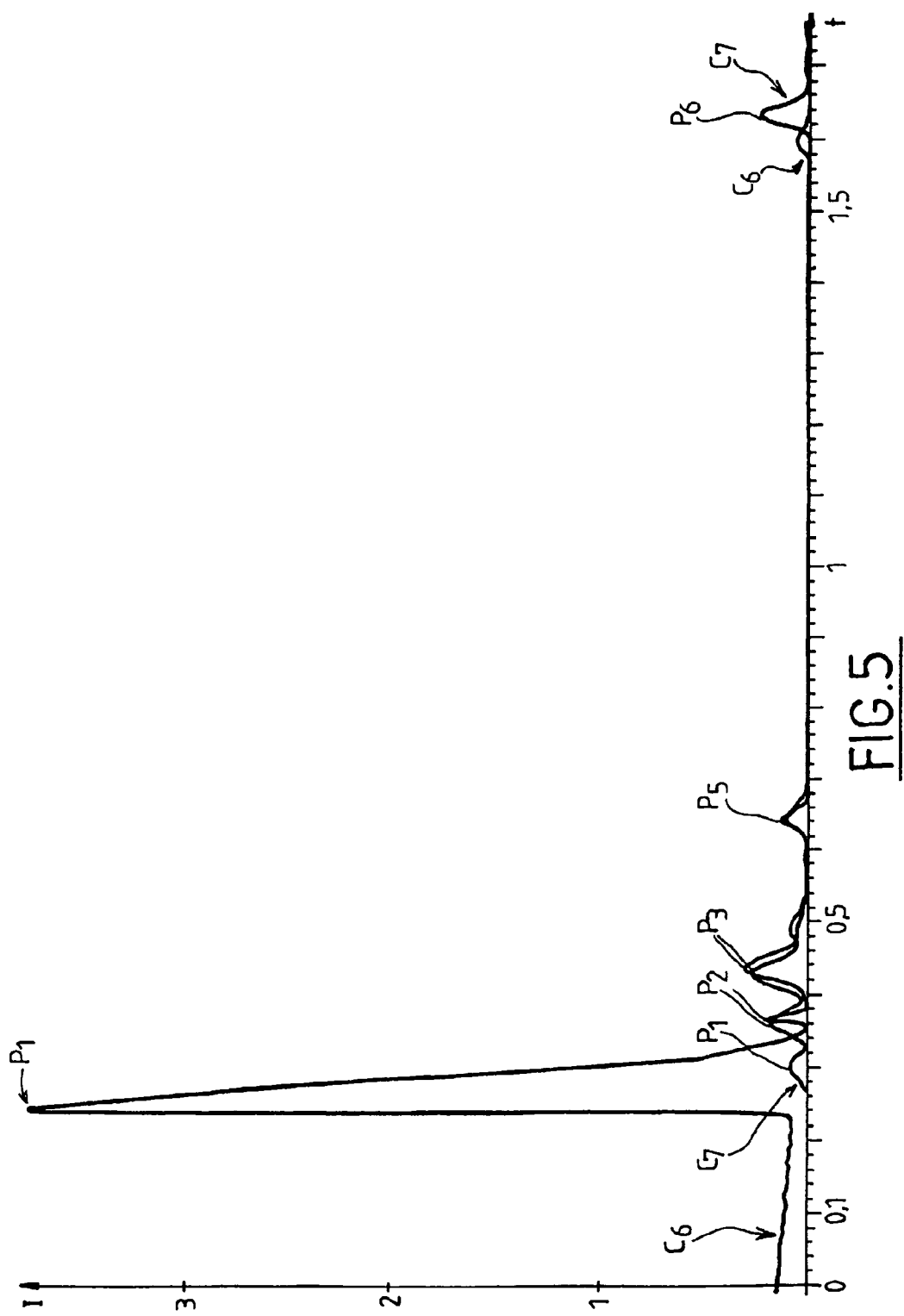
FIG. 5 is two superposed chromatograms of alveolar air taken respectively from an occasional smoker 5 minutes after smoking and from a chronic smoker at rest.

FIGS. 4 and 5 show that $C_2Cl_3F_3$ is also sensitive in revealing chemical type stress.

In FIG. 4, two chromatograms C5 (slightly offset) and C6 represent the alveolar air taken from an occasional smoker respectively at rest and 5 minutes after smoking.

The peaks P1 correspond again to the presence of $C_2Cl_3F_3$, the peaks P2 to the presence of isoprene, and the peaks P3 to the presence of dichloromethane. Other peaks are identified: the peak P6 corresponds to chloroform and the peak P12 to ethylether.

In FIG. 5, the two chromatograms comprising superposed curves C6 and C7 represent alveolar air taken respectively from the occasional smoker, 5 minutes after smoking as in the preceding figure, and for comparison from a chronic smoker at rest, who had not smoked for at least 1 hour prior to the sample being taken. In this Figure, the hexane peak P5 and the chloroform peak P6 of heptane are also shown.

A comparison between the peaks P1 in the two chromograms shows clearly that the biomarker of the invention, $C_2Cl_3F_3$, is a good marker of a temporary stress state but not of a chronic state. The quantity of $C_2Cl_3F_3$ was calibrated relative to dichloromethane which is present in alveolar air and which varies little, the calibration being in the form of the following ratio F between the intensities of the signals for the chromatograph peaks:

$$F = \frac{\text{chromatographic peak signal for biomarker}}{\text{chromatographic peak signal for dichloromethane}}$$

Such calibration F is summarized in the table below for various examples of stress states taken from a rest state, and in general 5 minutes after the end of various causes of stress (unless stated to the contrary), and specifically: physiological stress due to practicing sports (violent and moderate), biochemical stress due to smoking, psychic stress due to playing a fast video game intensely, and biophysical stress due to exposure to pulsed electromagnetic radiation from a computer screen.

The calibrated measurements F of the biomarker taken at rest ($F_0$) and after being subjected to various kinds of stress in the conditions stated, are summarized in the following table:

| Type of stress | $F_0$ | How applied | F |
|---|---|---|---|
| Moderate physical | 0.37 | 20 minutes exercise bicycle | 0.48 |
| Moderate physical | 0.13 | 15 minutes walking fast | 3.14 |
| Violent physical | 0.21 | 1 hour of tennis | 7.87 |
|  |  | 6 hours after the effort | 0.59 |
| Biochemical | 0.13 | Smoking a cigarette | 12.5 |
| Psychic | 0.37 | 30 minutes of intense playing of a fast video game | 5.00 |
| Biophysical | 0.21 | 30 minutes exposure to electromagnetic radiation from a computer screen | 0.88 |
|  |  | 15 minutes after the exposure | 0.44 |
|  |  | 90 minutes after the exposure | 0.21 |

Thus, whatever the type of stress, it is possible from the values obtained to quantify stress levels for each type of stress.

The invention is not limited to the examples described and shown. For example, the fluorine compound products may be used not only for prophylactic purposes but also for stress-curing purposes, at a determined dosage. Furthermore, the use of fluorine compounds as a preventative agent can be extended to endogenous fluorine compounds and to compounds suitable for mobilizing them.

What is claimed is:

1. A method for determining a calibration value for a biomarker for a stress state comprising the steps of:
    taking a first sample comprising a biological fluid of a person in a biological stress state;
    concentrating the first sample to obtain a first concentrated sample;
    analyzing the first concentrated sample by thermal desorption and then gas chromatography coupled with mass spectrometry, to obtain a first chromatographic peak signal for a biomarker for stress states which is a fluorinated chloroalkane; and
    obtaining a first calibration value by dividing the first chromatographic peak signal of the biomarker by a chromatographic peak of dichloromethane which is present in the biological fluid.

2. A method of quantitatively determining the stress level of a person comprising the steps of:
    taking a first sample comprising a biological fluid of a person in a biological stress state;
    concentrating the first sample to obtain a first concentrated sample;
    analyzing the first concentrated sample by thermal desorption and then gas chromatography coupled with mass spectrometry, to obtain a first chromatographic peak signal for a biomarker for stress states which is a fluorinated chloroalkane;
    obtaining a first calibration value by dividing the first chromatographic peak signal of the biomarker by a chromatographic peak of a reference compound which is present in the biological fluid of the first sample;
    taking a second sample of a biological fluid of the person in a resting state;
    concentrating the second sample to obtain a second concentrated sample;
    analyzing the second concentrated sample by thermal desorption and then gas chromatography coupled with mass spectrometry, to obtain a second chromatographic peak signal for a biomarker for stress states which is a fluorinated chloroalkane; and
    obtaining a second calibration value by dividing the second chromatographic peak signal of the biomarker by the chromatographic peak of a reference compound which is present in the biological fluid of the second sample; and
    quantitatively determining the stress level for the person by comparing the first and second calibration values.

3. A method according to claim 2, wherein the biological fluid is breath air.

4. A method according to claim 3, wherein the biological fluid is taken from a fraction of alveolar air obtained by air breathed out by a human body.

5. A method according to any one of claims 2 to 4, wherein the fluorinated chloroalkane is selected from the group consisting of trichloro-trifluro-ethane, tetrachloro-hexafluoro-butane, and trichloro-monofluoro-methane.

6. A method according to claim 2, wherein the reference compound is dichloromethane.

* * * * *